United States Patent [19]

Cregg et al.

[11] Patent Number: 5,204,252
[45] Date of Patent: Apr. 20, 1993

[54] CANDIDA TROPICALIS TRANSFORMATION SYSTEM

[75] Inventors: James M. Cregg; Martin A. Gleeson, both of San Diego, Calif.; Lisa Haas, New York, N.Y.; Stephen Picataggio, Santa Rosa, Calif.

[73] Assignee: Henkel Research Corporation, Santa Rosa, Calif.

[21] Appl. No.: 386,837

[22] Filed: Jul. 27, 1989

Related U.S. Application Data

[63] Continuation-in-part of Ser. No. 308,481, Feb. 8, 1989, abandoned.

[51] Int. Cl.$^5$ .................. C12N 15/52; C12N 15/63; C12N 15/81; C12N 1/19
[52] U.S. Cl. .................................. 435/255; 435/924; 435/172.3; 536/23.7
[58] Field of Search .............. 435/25.5, 254, 256, 435/320.1, 172.3, 69.1, 252.3, 924; 536/2.7; 935/28, 37, 69

[56] References Cited

U.S. PATENT DOCUMENTS 4,657,857 4/1987 Edens et al. .............. 435/172.2
4,735,901 4/1988 Kurtz et al. .............. 435/172.3

FOREIGN PATENT DOCUMENTS 173668 3/1986 European Pat. Off. .......... 435/69.1
183070 6/1986 European Pat. Off. .......... 435/69.1
226752 7/1987 European Pat. Off. .......... 435/69.1

OTHER PUBLICATIONS

Stroemnaes *J Bact* vol. 95(1) Jan 1968 pp. 197–200 "Use of nystatin to Eliminate Spontaneous revertants in Yeast".
Kelly et al. *Mol Cell Biol.* vol. 7(1) Jan. 1987 pp. 191–207 "Directed mutagenesis in Candida albicans, One-step gene disruption to isolate ura$^3$ mutants".
Gillum et al. *Mol Gen Genet.* vol. 198 pp. 179–182 "Isolation of the Candida albicans gene for oritidine 5'--phosphate decarboxylate by complementation . . . ".
Ditchburn et al. *J Gen. Microbiol* 1971 vol. 67 pp. 299–306 "The Differential Effects of Nystatin on Growth of Auxotrophic and Prototrophic".
Gaillardin *Chem Abst* vol. 77(23) No. 149584r 1971 "Physiological and genetic studies on yeasts of the genus Candida".
Watanabe et al. *Chem Abst* vol. 70(15) No. 65372n 1968 "Accumlation of orotic acid by an auxotrophic mutant of Candida tropicalis".
Roggenkamp et al., Mol. Gen. Genet (1986) 202:302–308; Gleeson et al., Jour. of Gen. Micro. (1986) 132:3458–3465; Ho et al., Biot. and Bioe. Symp. No. 14 (1984):295–301. Chem. Abstracts: 87–09888; 87–06118; 86–11140; 86–09803; 86–08303; 88–00638; 86–07488; 86–06612; 86–05040; 86–04633; 86–01575; 85–12532; 85–12356; 85–06258; 84–08469; and 83–02925.
*Strain and Species Identification by Restriction . . . Candida Species,* Journal of Bacteriology, Apr. 1987, pp. 1639–1643, Magee et al.
*The Genetics of Candida,* CRC Press, 1990, pp. 177–186, Kirsch et al.
*Genetics of Candida albicans,* Microbiological Reviews, Sep. 1990, pp. 226–241, Scherer et al.
*Isolation and Determination of Yeasts . . . Source of Carbon,* Agr. Biol. Chem., vol. 30, No. 12, pp. 1175–1182, 1966, Tanabe et al.

(List continued on next page.)

Primary Examiner—Richard A. Schwartz
Assistant Examiner—John LeGuyader
Attorney, Agent, or Firm—Ernest G. Szoke; Wayne C. Jaeschke; John E. Drach

[57] ABSTRACT

A transformation system is provided for *C. tropicalis,* comprising constructs and microorganisms, as well as methods for preparing constructs and microorganisms, and transforming microorganisms. Particularly, a yeast transformation system comprising auxotrophic hosts which are auxotrophic in either an amino acid, purine or pyrimidine pathways and employ DNA constructs comprising genes encoding biosynthetic enzymes which functionally complement the auxotrophies to prototrophies.

9 Claims, 8 Drawing Sheets

OTHER PUBLICATIONS

*Methods for the Genetics and Molecular Biology of Candida albicans*, Analytical Biochemistry, 175, pp. 361–372 (1988), Magee et al.

*The Genus Candida Berkout nom. conserv.–... Delimitation*, System. Appl. Microbiol. 12, pp. 183–190 (1989), Viljoen et al.

*Variation in the electrophoretic karyotype... in Candida albicans*, Journal of General Microbiology (1990), 136, pp. 2433–2442, Iwaguchi et al.

*The Carboxyl-terminal Tripeptide Ala-Lys-Ile... Yeast Peroxisomes*, The Journal of Biological Chemistry, vol. 266, No. 34, pp. 23197–23208, 1991, Aitchison et al.

*In vivo import of Candida tropicalis... Candida albicans*, Current Genetics, 1990, 17:481–486, Aitchison et al.

*Redefinition of Candida berkhour and the consequent emendation of Cryptococcus kuetzing and Rhodotorula harrison*, accepted Mar. 31, 1988, Weijman et al.

*Interspecific Complementation Analysis... Candida albicans Adenine Auxotrophs*, Journal of Bacteriology, Jun. 1989, vol. 171, No. 6, pp. 3586–3589, Corner et al.

*Sequence and transcript analysis... -phosphate decarboxylase*, Curr Genet (1989), 16:153–157, Losberger et al.

*The yeasts: A taxonomic study*, third edition 1984, Elsevier Science Publishers B. V.–Amsterdam, N. J. W. Kreger-van Rij, ed., pp. 585–613 and 818–821.

*Differential Identification of Candida Species... Polypeptide Profiles*, Analytical Biochemistry 175, 548–551 (1988), Shen et al.

```
       -160              -140              -120
    CAAAGTAAGGATACAGATTTATACAATAAATTGCCATACTAGTCACGTGAGATATCTC

-100              -80               -60
    ATCCATTCCCCAACTCCCAAGAAAAAAAAAAAGTGnAAAAAAAAAATCAAACCCAAAGATC

-40               -20                1
    AACCTCCCCATCATCATCGTCATCAAACCCCAGCTCAATTCGCAATGGTTAGCACAAAA
                                                   MetValSerThrLys
        20                40                60
    ACATACACAGAAAGGGCATCAGCACACCCCTCCAAGGTTGCCCAACGTTTATTCCGCTTA
    ThrTyrThrGluArgAlaSerAlaHisProSerLysValAlaGlnArgLeuPheArgLeu 80                100               120
    ATGGAGTCCAAAAAGACCAACCTCTGCGCCTCGATCGACGTGACCACAACCGCCGAGTTC
    MetGluSerLysLysThrAsnLeuCysAlaSerIleAspValThrThrThrAlaGluPhe 140                160               180
    CTTTCGCTCATCGACAAGCTCGGTCCCCACATCTGTCTCGTGAAGACGCACATCGATATC
    LeuSerLeuIleAspLysLeuGlyProHisIleCysLeuValLysThrHisIleAspIle 200                220               240
    ATCTCAGACTTCAGCTACGAGGGCACGATTGAGCCGTTGCTTGTGCTTGCAGAGCGCCAC
    IleSerAspPheSerTyrGluGlyThrIleGluProLeuLeuValLeuAlaGluArgHis 260                280               300
    GGGTTCTTGATATTCGAGGACAGGAAGTTTGCTGATATCGGAAACACCGTGATGTTGCAG
    GlyPheLeuIlePheGluAspArgLysPheAlaAspIleGlyAsnThrValMetLeuGln 320                340               360
    TACACCTCGGGGGGTATACCGGATCGCGGCGTGGAGTGACATCACGAACGCGCACGGAGTG
    TyrThrSerGlyValTyrArgIleAlaAlaTrpSerAspIleThrAsnAlaHisGlyVal 380                400               420
    ACTGGGAAGGGCGTCGTTGAAGGGTTGAAACGCGGTGCGGAGGGGGTAGAAAAGGAAAGG
    ThrGlyLysGlyValValGluGlyLeuLysArgGlyAlaGluGlyValGluLysGluArg 440                460               480
    GGCGTGTTGATGTTGGCGGAGTTGTCGAGTAAAGGCTCGTTGGCGCATGGTGAATATACC
    GlyValLeuMetLeuAlaGluLeuSerSerLysGlySerLeuAlaHisGlyGluTyrThr 500                520               540
    CGTGAGACGATCGAGATTGCGAAGAGTGATCGGGAGTTCGTGATTGGGTTCATCGCGCAG
    ArgGluThrIleGluIleAlaLysSerAspArgGluPheValIleGlyPheIleAlaGln
```

FIG. 3

```
                560                    580                    600
         CGGGACATGGGGGGTAGAGAAGAAGGGTTTGATTGGATCATCATGACGCCTGGTGTGGGG
         ArgAspMetGlyGlyArgGluGluGlyPheAspTrpIleIleMetThrProGlyValGly 620                    640                    660
         TTGGATGATAAAGGCGATGCGTTGGGCCAGCAGTATAGGACTGTTGATGAGGTGGTTCTG
         LeuAspAspLysGlyAspAlaLeuGlyGlnGlnTyrArgThrValAspGluValValLeu 680                    700                    720
         ACTGGTACCGATGTGATTATTGTCGGGAGAGGGTTGTTTGGAAAAGGAAGAGACCCTGAG
         ThrGlyThrAspValIleIleValGlyArgGlyLeuPheGlyLysGlyArgAspProGlu 740                    760                    780
         GTGGAGGGAAAGAGATACAGGGATGCTGGATGGAAGGCATACTTGAAGAGAACTGGTCAG
         ValGluGlyLysArgTyrArgAspAlaGlyTrpLysAlaTyrLeuLysargThrGlyGln 800                    820                    840
         TTAGAATAAATATTGTAATAAATAGGTCTATATACATACACTAAGCTTCTAGGACGTCAT
         LeuGluEnd 860                    880                    900
         TGTAGTCTTCGAAGTTGTCTGCTAGTTTAGTTCTCATGATTTCGAAAACCAATAACGCAA 920                    940                    960
         TGGATGTAGCAGGGATGGTGGTTAGTGCGTTCCTGACAAACCCAGAGTACGCCGCCTCAA 980                   1000                   1020
         ACCACGTCACATTCGCCCTTTGCTTCATCCGCATCACTTGCTTGAAGGTATCCACGTACG

1040
         AGTTGTAATACACCTTGAAGAA
```

FIG.3a

```
        -20                    1                  20
ATAATCTTCACCAAACACCCAGCTCAATTCACCATGGTTAACACACAAACATACACAGCA
                                  MetValAsnThrGlnThrTyrThrAla 40                   60                  80
AGGGCATCAAGGCACCCCTCCAAGGTCGCCCAACGTTTATTTCGCTTAATGGAGTCCAAA
ArgAlaSerThrHisProSerLysValAlaGlnArgLeuPheArgLeuMetGluSerLys 100                  120                 140
AAGACCAACCTCTGTGCCTCGATCGACGTGACCACGACCGCCGAGTTCCTTTCACTCATC
LysThrAsnLeuCysAlaSerIleAspValThrThrThrAlaGluPheLeuSerLeuIle 160                  180                 200
GACAAGCTCGGTCCCTACATTTGTCTCGTGAAGACGCACATCGACATCATTTCGGACTTC
AspLysLeuGlyProTyrIleCysLeuValLysThrHisIleAspIleIleSerAspPhe 220                  240                 260
AGCTACGAGGGCACAATCGAGCCGTTGCTTGCGCnnTCGCGGAgccACGGGTTCTTGATC
SerTyrGluGlyThrIleGluProLeuLeuAlaXxxSerArgSerHisGlyPheLeuIle 280                  300                 320
TTTGAAGATAGGAAGTTTGCGGATATCGGAAACACCGTGATGTTGCAGTACACCTCGGGG
PheGluAspArgLysPheAlaAspIleGlyAsnThrValMetLeuGlnTyrThrSerGly 340                  360                 380
GTGTATCGGATCGCGTCGTGGAGTGACATCACGAACGCGCACGGTGTGACTGGGGCAGGT
ValTyrArgIleAlaSerTrpSerAspIleThrAsnAlaHisGlyValThrGlyAlaGly 400                  420                 440
GTTGTTGAAGGGTTGAAGCnGCGGCCGGAGGAGGTAGAAGGAAGAGAAAGGGGCGTGTTG
ValValGluGlyLeuLysXxxArgProGluGluValGluGlyArgGluArgGlyValLeu 460                  480                 500
ATGTTGGCGGAGTTGTCAAGTAAAGGCTCGTTGGCGCATGGCGAATATCCCCGTGAGACG
MetLeuAlaGluLeuSerSerLysGlySerLeuAlaHisGlyGluTyrProArgGluThr 520                  540                 560
ATCGAGATTGCGAAGAGTGATCGTGAGTTCGTGATTGGGTTCATTGCGCACGGGGACATG
IleGluIleAlaLysSerAspArgGluPheValIleGlyPheIleAlaHisGlyAspMet 580                  600                 620
GGGGGTAGAGAAGAAGGGTTTGATTGGATCATCATGACGCCTGGCGTGGGGTTGGATGAT
GlyGlyArgGluGluGlyPheAspTrpIleIleMetThrProGlyValGlyLeuAspAsp 640                  660                 680
AAAGGGGATGCGTTGGGCCAGCAGTATAGGACTGTTGATGAGGTGGTTCTGACTGGTACG
LysGlyAspAlaLeuGlyGlnGlnTyrArgThrValAspGluValValLeuThrGlyThr
```

FIG. 4

```
                    700                        720                        740
GATGTGATTATTGTCGGGAGAGGGTTGTTTGGGAAAGGAAGAGACCCTGAGGTGGAGGGA
AspValIleIleValGlyArgGlyLeuPheGlyLysGlyArgAspProGluValGluGly 760                        780                        800
AAGAGATATAGAGATGCCGGATGGAAGGCATACTTGAAGAGAACCGGTCAGTTAGAATAA
LysArgTyrArgAspAlaGlyTrpLysAlaTyrLeuLysArgThrGlyGlnLeuGluEnd 820                        840                        860
ATATTGTAATAAATAGGTCTATATACATAGGCTAAGCTTCTAGGACGTCATTGTAGTCTT

CGAAGT
```

FIG. 4a

```
  1  GTTCCACCGG GAAATTGACC CCTGAAGTTG TCTACGTCGC CCACAAACTC
 51  GGTGCCAAGT GCATCGTGAT GGCTGGTGGT GCTCAAGCTG TCAcCGCTAT
101  GGCTTACGGT ACTGAGAGCG TCATTAAATG TGACAAGATC TTGGGTCCAG
151  GTAACCAGTT CGTCACTGCT GCCAAGATGT ACGTGCAGAA CGATACCCAA
201  GCTTTATGTT CCATCGACAT GCCTGCTGGT CCTTCTGAAG TCTTGGTTAT
251  TGCTGATTCC CAcGCCGATG CTGATTTCGT TGCCAGTGAC TTGCTTTCAC
301  AAGCTGAACA TGGaGTCGAC
```

```
   1  STGKLTPEVVYVAHKLGAKCIVMAGGAQAVTAMAYGTESVIKCDKILGPG   50
 519  SDGKVSPEVVYVAEKVGASKIVLAGGAQAVAAMAYGTETIPKVDKILGPG  568

51  NQFVTAAKMYVQNDTQALCSIDMPAGPSEVLVIADSHADADFVASDLLSQ  100
 569  NQFVTAAKMYVQNDTQALCSIDMPAGPSEVLVIADEDADVDFVASDLLSQ  618

101  AEHGVD  106
 619  AEHGID  624
```

```
 312  GGGAAATTGACCCCTGAAGTTGTCTACGTCGCCCACAAACTCGGTGCCAA  263
2892  GGTAAAGTTTCACCCGAAGTTGTTTATGTCGCAGAAAAAGTTGGCGCTTC  2941

262  GTGCATCGTGATGGCTGGTGGTGCTCAAGCTGTCACCGCTATGGCTTACG  213
2942  CAAGATTGTTCTAGCTGGTGGTGCCCAAGCCGTTGCTGCTATGGCTTACG  2991

212  GTACTGAGAGCGTCATTAAATGTGACAAGATCTTGGGTCCAGGTAACCAG  163
2992  GGACAGAAACTATTCCTAAAGTGGATAAGATCTTGGGTCCAGGTAATCAA  3041

162  TTCGTCACTGCTGCCAAGATGTACGTGCAGAACGATACCCAAGCTTTATG  113
3042  TTTGTGACTGCCGCCAAAATGTATGTTCAAAATGACACTCAAGCTCTATG  3091

112  TTCCATCGACATGCCTGCTGGTCCTTCTGAAGTCTTGGTTATTGCTGATT   63
3092  TTCCATTGATATGCCAGCTGGCCCAAGTGAAGTTTTGGTTATTGCCGATG  3141

62  CCCAcGCCGATGCTGATTTCGTTGCCAGTGACTTGCTTTCACAAGCTGAA   13
3142  AAGATGCCGATGTGGATTTTGTTGCAAGTGATTTGCTATCGCAAGCTGAA  3191

12  CATGGaGTCGAC   1
3192  CACGGTATTGAC  3203
```

FIG. 6

CANDIDA TROPICALIS TRANSFORMATION SYSTEM

CROSS REFERENCE TO RELATED APPLICATIONS

This application is a continuation-in-part of application Ser. No. 07/308,481 filed Feb. 8, 1989, now abandoned, the contents of which are fully incorporated herein by reference.

BACKGROUND OF THE INVENTION

1. Field of the Invention

This invention relates to a process for transformation of the alkane- and fatty acid-utilizing yeast of *Candida tropicalis* for industrial purposes. The transformation process described herein provides a means to introduce DNA fragments or sequences into host cells of *C. tropicalis* and allows *C. tropicalis* to be used as a host system for (1) gene expression and (2) polypeptide and protein production. Transformed yeast cells can be identified and selected by the methods of the present invention. Novel strains of *C. tropicalis*, vectors and subclones are provided. Novel yeast strains are used as hosts for introduction of recombinant DNA fragments.

The invention further relates to methods for stable transformation and maintenance of DNA in host cells. DNA is integrated into the genome by homologous recombination and both single and multiple tandem integrations are observed.

2. Description of the Related Art

There has been a continuing interest in developing important industrial eukaryotic micro-organisms for the production of a wide variety of products. In many cases, bacterial systems, such as *E. coli* or *Bacillus* are convenient and satisfactory, but for many purposes prokaryotic systems are inadequate. Prokaryotes do not provide processing of their peptides, such as glycosylation. In addition, prokaryotes do not efficiently secrete products. Products prepared in prokaryotes normally require cell lysis and then isolation of the proteins in the presence of large amounts of bacterial proteins and cellular debris. Prokaryotes have severe limitations for post-translational modifications and for production of products which can be isolated from the nutrient medium.

Yeast provide an attractive alternative to prokaryotes as host organisms. They can be used for large scale fermentations and are adaptable to continuous fermentation processing. In addition, they are not susceptible to phage infection and generally require only semi-sterile conditions. Conveniently, these cells may be immobilized for the production of metabolites and enzymes.

For some purposes, biochemical properties of yeast may be similar to higher organisms. For example, yeast may provide for glycosylation of polypeptide products. In addition, as eukaryotic organisms, the yeast codon preference may be similar to the codon preference of the organism from which the gene has been isolated. This may result in higher efficiencies of production of the desired protein. In addition, yeast are able to secrete proteins into the nutrient medium, which proteins can be readily recovered by conventional methods.

A number of yeast strains have been used as host organisms for recombinant gene expression. Lack of information about transformation conditions and appropriate vectors of *C. tropicalis* precluded development of a host/vector system for this yeast. Auxotrophic mutants were not available for *C. tropicalis*, thus preventing direct selection for transformants by auxotrophic complementation. The present invention overcomes such problems. The invention provides (1) a recombinant transformation system for *C. tropicalis*; (2) host strains, vectors and subclones for the transformation system; (3) methods for selection and identification of cells containing introduced DNA; (4) and methods to grow and maintain stably transformed cells. Further, genetically engineered *C. tropicalis* mutants may provide a means to screen chemical compounds for antifungal activity. A sensitive screening procedure for compounds toxic to this microorganism or related microorganisms (i.e., *Candida albicans*) would be of interest to the medical community.

RELEVANT LITERATURE

Transformation of the yeast *Hansenula polymorpha* is described by Roggenkamp et al., *Mol. Gen. Genet.* (1986) 202:302–308; Gleeson et al., *J. Gen. Micro.* (1986) 3459–3465. Transformation of *Saccharomyces* may be found in EPA Serial No. 0,173,668. Transformation of the genus Pichia may be found in EPA Serial No. 0,183,070. Transformation of *Kluyveromyces* is described in U.S. Pat. No. 4,657,857. A preliminary cloning system for *Candida utilis* is found in Ho et al., *Biotechnology and Bioengineering Symo.* No. 14 (1984) :295–301. References associated with use of Candida species for cloning or other purposes include U.S. Pat. No. 4,735,901; Kawai et al., *Agric. Biol. Chem.* (1987) 51:1587–91; Japanese Patent Application numbers 87-133259 and 87-133260; Hamasawa et al., *J. Gen. Microbiol.* (1987) 133:1089–97; Takagi et al., *J. Bacteriol.* (1986) 167:551–55; Kurtz et al., *Mol. Cell. Biol.* (1986) 6:142–49; Davidow et al., *Curr. Genet.* (1985) 10:39–48; Tikhomirova et al., *Curr. Genet.* (1986) 10:741–47; Kunze et al., *Acta Biotechnol.* (1986) 6:28; Kohchi, et al., *Mol. Gen. Genet.* (1986) 203:89–94; Cohen et al., *Mol. Biol. Yeast* (1985) 345; Kurtz et al., *Mol. Biol. Yeast* (1985) 67; Sugisaki et al., *J. Bacteriol.* (1985) 164:1373–75; Kunze et al., *J. Basic Microbiol.* (1985) 25:141–44; Kohchi, *Nucleic Acids Res.* (1985) 13:6273–82; Kunze et al., *Curr. Genet.* (1985) 205–09; Stevis et al., *Fed. Proc. Fed. Am. Soc. Exp. Biol.* (1984) 43:1699; Lidstrom, *Biotechnol. Bioeng.* (1984) Symp. 13:329–44; Hsu et al., *Abstr. Annu. Meet. Am. Soc. Microbiol.* (1983) 83 Meet. 136.

EPA Serial No. 0,226,752 describes the site-selective genomic modification of yeast of the genus Pichia.

SUMMARY OF THE INVENTION

Processes and compositions are provided for transformation of *Candida tropicalis* for use as an industrial microorganism and as a clinical research tool. *C. tropicalis* host cells, vectors and subclones and a transformation system for introducing DNA into the *C. tropicalis* host are provided. Host cells are selected which stably maintain introduced DNA. In particular, metabolic mutants are provided that are made prototrophic with introduced DNA. The invention further relates to a selectable marker system composed of metabolic mutants which are made prototrophic by introduction of biosynthetic genes which functionally complement the host defects.

BRIEF DESCRIPTION OF THE FIGURES

The present invention may be more fully understood by reference to the following detailed description of the invention examples of specific embodiments of the invention, and appended figures.

FIG. 3 (parts 3 and 3a) shows the DNA sequence of the C. tropicalis URA3A gene.

FIG. 4 (parts 4 and 4a) shows the DNA sequence of the C. tropicalis URA3B gene.

FIG. 6 shows a partial DNA sequence of the C. tropicalis HIS4 gene and comparison to the DNA sequence of the C. cerevisiae HIS4 gene.

DESCRIPTION OF THE SPECIFIC EMBODIMENTS

Figure 1:
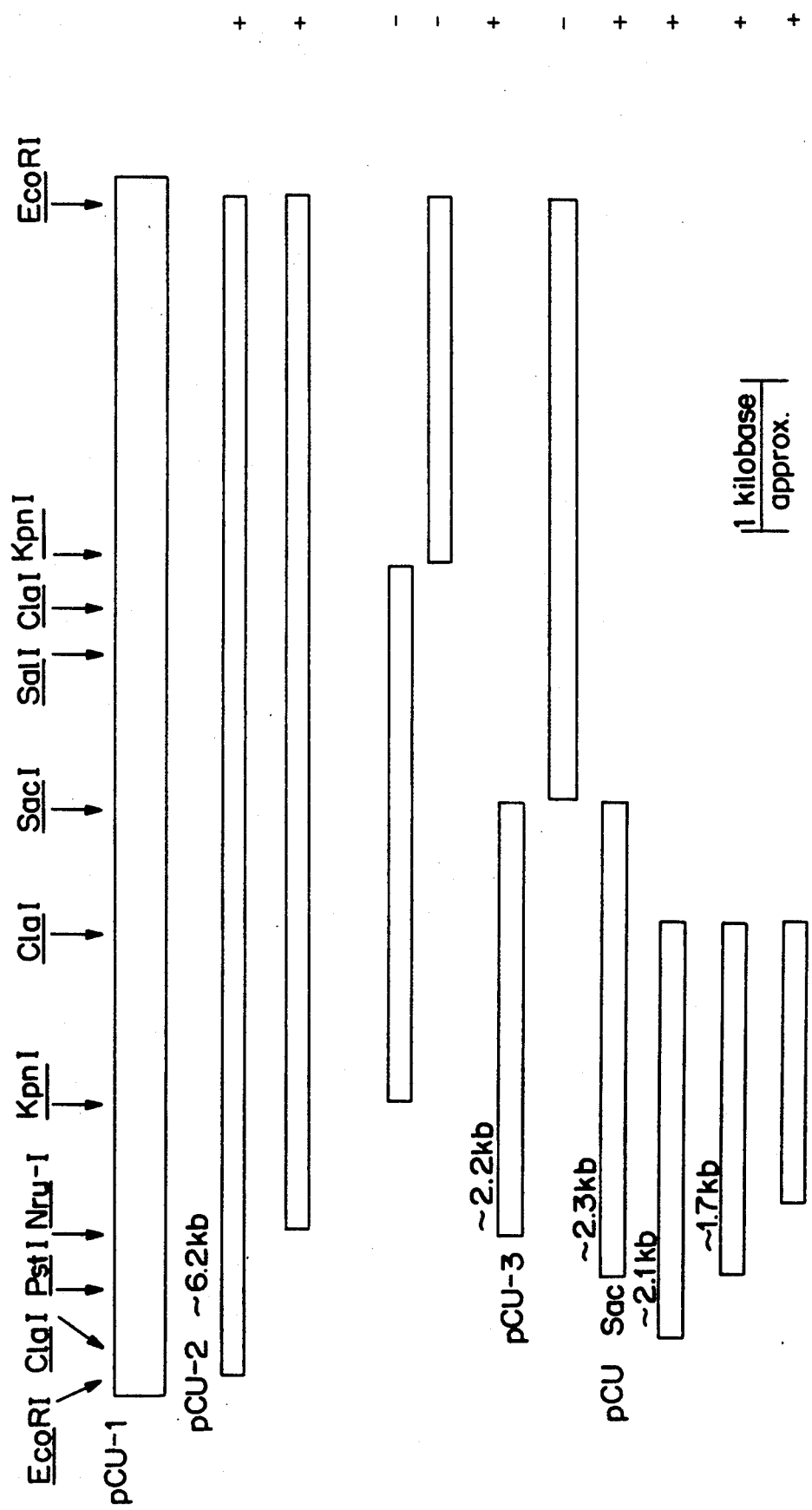
FIG. 1 shows the restriction map of C. tropicalis URA3A gene in pCUI (top) and a representation of the C. tropicalis DNA fragments used to transform C. tropicalis and S. cerevisiae ura3 strains SU-2 and SHY3, respectively. A (+) symbol indicates that the fragment transformed the indicated strain, whereas a (−) symbol indicates that transformation did not occur.

Other than in the operating examples, or where otherwise indicated, all numbers expressing quantities of ingredients or reaction conditions used herein are to be understood as modified in all instances by the term "about".

Compositions are provided comprising host strains and constructs as components of a system employing Candida tropicalis mutants as hosts for introduction of nucleic acids. Particularly, Candida tropicalis prototrophs are modified to provide for an auxotroph in a metabolic pathway, which can be complemented by the introduction of one or more genes of the defective metabolic pathway complementing the defect. The mutant will be defective in at least one metabolic pathway and may be defective in additional metabolic pathways. Usually, from one to two genes will have been mutated resulting in a substantial block or total block of the production of the particular metabolite. The strain will have a low frequency of reversion, generally a frequency of less than about $10^{-6}$ more usually a frequency of less than about $10^{-7}$. Thus, these cells may be considered to be "tight" and their requirement for the metabolite or metabolic intermediate, may be considered to be an absolute need for the metabolic intermediate or metabolite. Desirably, the cells will not be leaky, so that the production of the metabolite will be totally absent.

The metabolic pathways to which defects may be introduced will be primarily amino acids, purines and pyrimidines. Of these biosynthetic pathways, the ones of particular interest include uracil, histidine, adenine, proline, methionine, cysteine and lysine, particularly uracil and histidine.

A number of ways exist for introducing a defect into a metabolic pathway. One method which has been shown to be successful includes the use of either chemical or physical mutagenesis to provide for mutants which demonstrate a defect in a particular metabolic pathway. The efficiency of the selection process for the desired mutants can be substantially enhanced by growing the mutants in a medium which is cytotoxic for rapidly dividing cells so as to select against prototrophic cells. Conveniently, a cytotoxic level of nystatin, or other cytotoxic agents such as hygromycin, bleomycin, copper, etc. may be employed in this selection process. The concentration for nystatin will generally be in the range of about 15-50 units/ml. The mutagenized cells will be grown in conventional defined yeast media in the presence of nystatin to enhance the proportion of auxotrophs resulting from the mutagenesis.

A wide variety of mutagenic agents may be employed, which include nitrosoguanidine, ethyl methanesulfonate, sulfur or nitrogen mustards, ultraviolet radiation, x-ray radiation, etc. In particular, the chemical agent nitrosoguanidine has been found to be effective in the present invention. While growth in the presence of an agent cytotoxic for rapidly dividing cells is desirable, it is not essential.

The mutagenized cells are then screened for the particular metabolic defect. Of particular interest is a URA3 gene defect, since it allows for both positive and negative selection The cells may be screened for uracil mutants, since C. tropicalis is sensitive to the uracil pathway intermediate analog 5-fluoroorotic acid (5FOA) Mutants defective in the URA5 or URA3 genes will not metabolize this analog to a toxic product and so will survive growth on medium containing 5FOA. However, cells surviving cytotoxic levels of 5FOA may survive not only as a result of URA3 or URA5 defects, but also as a result of defects of uptake enhanced transport from the cytoplasm or other mechanism which may be involved with reducing the effectiveness of the 5FOA.

To reduce the proportion of this class of uracil requiring mutants, a double selection regime may be carried out. Mutagenized cells are enriched for auxotrophs as described above, followed by challenging the defective mutants with a 5FOA-containing medium supplemented both with uracil and uridine. Since uridine is more soluble than uracil, the uridine may be added in relatively high concentrations, where the organism has a poor uracil uptake system. The level of 5FOA will generally be in the range of about 300-1000 mg/L, preferably in the range of about 500-700 mg/L. Uracil will generally be present in from about 25-75 mg/L and one or both of uridine or uridine monophosphate will be present in a total amount of about 200-500 mg/L. For selection, the cell concentration will generally range from about 0.1 to 25 $A_{600}$ The incubation will normally be at least about two days and may be as long as ten days at a temperature of about 30° C. The selection procedure may be repeated one or more times.

The selected mutant cells which are defective in the uracil biosynthetic pathway may then be isolated and assayed for orotidine-5'-phosphate decarboxylase activity, which is the URA3 gene product, in accordance with conventional procedures.

The auxotrophs found to be defective for orotidine 5-phosphate decarboxylase activity are then screened for reversion frequency, with cells having reversion frequencies of greater than about $10^{-6}$ being rejected As part of the system employing C. tropicalis for production of a variety of products, DNA constructs will be employed for introduction into the host by any convenient means. Techniques for introduction of DNA into the host include transformation, fusion, electroporation, or the like. Depending upon the method of transformation, whole cells or spheroplasts may be employed. In carrying out the transformation, use of spheroplasts has been found to be effective with the subject host cells. Conveniently, the cells are harvested and spheroplasts prepared in accordance with conventional techniques, for example using zymolyase. Other enzymes which degrade the cell wall, may also be used, such as lyticase, glusulase, etc. The cells are suspended in an appropriate isotonic buffer, e.g., 1M sorbitol and the cell wall degraded with the appropriate enzyme system. The resulting spheroplasts are maintained in an appropriate isotonic medium prior to transformation.

For transformation, the spheroplasts and appropriate DNA sequences are introduced into a convenient fusogen containing medium e.g. polyethylene glycol, at a concentration of about 15–30%, with a molecular weight of the polyethylene glycol from about 2,000 to 6,000, preferably from about 3,000 to 4,000. After incubation for at least about 10 min. at room temperature, samples may be centrifuged, and the spheroplasts resuspended in isotonic medium.

The spheroplast preparation is then regenerated employing an agar medium containing yeast nitrogen base, glucose, dextrose and isotonic buffer. The spheroplasts are suspended in melted regeneration agar which is poured as a layer onto the regeneration agar medium. Alternatively, the LiCl whole cell transformation method can be used (Ito, H. et al., (1983). *J. Bacteriol.* 153:163–168).

Transformation is achieved by site-specific integration of DNA into the yeast genome by homologous recombination. Transformation occurs with circular or linear DNA, by homologous integration, in either single or multiple copy, or by gene replacement. Stable integration is economically desirable for industrial purposes since neither expensive supplements nor defined media are generally required to maintain the DNA. In addition, multiple tandem integration may provide a means to increase the level of expressed gene products.

The following examples are offered by way of illustration and not by way of limitation.

EXPERIMENTAL

1. Development of Mutants a. Mutagenesis

*C. tropicalis* (ATCC 20336) wildtype cells derived from a single colony were grown in 200 ml of YEPD medium (yeast extract 10 g/L, dextrose 20 g/L, peptone 20 g/L) to an $A_{600}$ of 0.5. The cells were harvested by centrifugation at 3,000 rpm for 5 minutes (Damon IEC centrifuge, IEC 153 rotor) and washed once in sterile distilled water and twice with 50 ml of citrate buffer (100 mM sodium citrate, pH 5.5). The cells were then suspended in 10 ml of citrate buffer. Nitrosoguanidine (NTG; 10 mg/ml solution in citrate buffer; Sigma #M7629) was added to the culture to a final concentration of 100 μg/ml. The culture was then incubated with NTG at room temperature in a ventilation hood for 30 min. without shaking. After incubation, the culture was washed three times with sterile distilled water and aliquoted into 5 flasks containing 100 ml YEPD medium. These cultures were incubated for 3 hours at 30° C. with shaking (200 rpm).

The mutagenized cells were either subjected to mutant screening directly, as follows, or subjected to nystatin enrichment, or stored in YEPD glycerol (YEPD+40% glycerol) at −70° C. after centrifugation harvesting of cells and re-suspension in 2 ml of YEPD glycerol.

b. Nystatin enrichment

A mutagenized culture of cells was washed in sterile distilled water and inoculated to a starting $A_{600}$ of 0.4 into 100 ml of yeast carbon base (YCB; 11 g/L;DDifco) in a sterile 500 ml flask. The culture was shaken at 200 rpm for 15 hours at 30° C. The cells were then centrifuged (3000× g, 5 min) and resuspended in 100 ml of minimal medium (yeast nitrogen base 6.7 g/L, dextrose 20 g/L) in 500 ml flasks. The cells were incubated with shaking (200 rpm) at 30° C. for 7 hours. Then, nystatin (50,000 units/ml stock solution in methanol; Sigma #N3503) was added at a final concentration of 35 units/ml and the cells incubated for 35 minutes at 30° C. with shaking (200 rpm). The culture was washed twice with sterile distilled water and resuspended in 10 ml of sterile distilled water. The culture was then placed onto YEPD plates incubated for 2 days at 30° C. and replica plated to minimal medium (YNB-0.67%, dextrose-2%) and YEPD plates. These were incubated for 2 days at 30° C. and then scored for lack of growth on minimal plates. Non-growing patches on the minimal plates were subcultured from the corresponding YEPD replica plate and were the subject of further analysis.

c. Partial Characterization of Auxotrophic Mutants

Mutants isolated in the above experiments were characterized as to growth requirements using standard methods (Sherman et al., Methods in Yeast Genetics, 1979). Mutants were transferred onto sets of YEPD plates according to a pattern. After growth on YEPD agar, the cell patches were replica-plated onto a set of minimal plates each supplemented with a single amino acid, purine or pyrimidine. After incubation of the colonies for 2 days at 30° C. the pattern of growth for each strain was observed and a tentative identification of a single growth factor requirement was made. The specific growth requirement of each mutant was confirmed by streaking the mutant onto YNB agar plates supplemented with all but one nutrient. Finally, to ensure that the mutants were *C. tropicalis,* several mutant strains of each type were examined microscopically and phenotypically for ability to utilize n-decane as sole carbon and energy source.

Mutants which showed complex growth patterns on the pool plates or which were too "leaky" to identify were eliminated from consideration. A total of 194 mutants in six different auxotrophic classes was observed. More than 50% of the mutants required adenine for growth, and 20% required either methionine or cysteine. Many pathways were not represented in this collection. It is reasonable to assume that many of these strains, which have the same nutrient requirement, are defective in the same gene.

Of the 106 adenine-requiring strains, 8 displayed a pink or red colony color, similar to *C. cerevisiae* mutants defective in either the ADE1 or ADE2 gene products, PR-aminoimidazolesuccino-carboxamide synthase and PR-aminoimidazole-carboxylase, respectively.

2. Isolation of SU-1 and SU-2 Auxotrophic Mutants a. Nystatin enrichment

A mutagenized culture of cells was washed in sterile distilled water and inoculated to a starting $A_{600}$ of 0.4 into 100 ml of yeast carbon base (YCB; 11 g/L; Difco) in a sterile 500 ml flask. The culture was shaken at 200 rpm for 15 hours at 30° C. The cells were then centrifuged (3000 ×g, 5 min) and resuspended in 100 ml of minimal medium (yeast nitrogen base 6.7 g/L, dextrose 20 g/L) in 500 ml flasks. The cells were incubated with shaking (200 rpm) at 30° C. for 7 hours. Then, nystatin (50,000 units/ml stock solution in methanol; Sigma #N3503) was added at a final concentration of 35 units/ml and the cells incubated for 35 minutes at 30° C. with shaking (200 rpm). The culture was washed twice with sterile distilled water and resuspended in 10 ml of sterile distilled water.

b. Selection

Nystatin-treated cells (0.1 ml aliquots) were plated onto five selection plates (YNB 6.7 g/L, dextrose 20 g/L, agar 20 g/L, uracil 50 mg/L, uridine 150 mg/L, uridine 5-phosphate 150 mg/L, 5-fluoroorotic acid 500 mg/L) at a range of cell concentrations (20 $A_{600}$, 2 $A_{600}$ and 0.2 $A_{600}$ of cells). The plates were incubated for six days at 30° C., at which time they were scored Colonies which grew on the plates were picked with sterile toothpicks and plated onto a second set of selection plates prepared as before Incubation was for four days at 30° C.

c. Screening

The plates were then replica plated to minimal plates with or without uracil. Colonies which could not grow in the absence of uracil were taken for further analysis The cells were assayed for orotidine 5'-phosphate decarboxylase (URA3 gene product) activity as follows:

Cells to be tested were grown in 200 ml YEPD at an $A_{600}$ of 2.0. Cells were harvested by centrifugation at 2000 rpm and washed in potassium phosphate buffer (0.1 M, pH7.5, 5 mM 2-mercaptoethanol). To 1 g of cells was added 1 g of glass beads, 0.5 mm diameter. The mixture was vigorously vortexed for 5 min. One ml of buffer was added and the mix was again vortexed for 5 min. One ml of cell extract was centrifuged at 20,000 rpm for 40 minutes in a Sorvall RC-5B refrigerated super speed centrifuge, SS34 rotor. Supernatant was removed and passed through a G25 Sephadex column. The resulting cell extract was then assayed for orotidine-5'-phosphate decarboxylase activity.

Orotidine-5'-phosphate decarboxylase was assayed by the method of Yoshimoto et al., *Meth. in Enzymology* (1978) 51:74–79. Addition of cell extract was standardized by setting the background reading $A_{290}$ to 0.4 in typically 10–20 ul/3 ml cuvette. Addition of substrate, orotidine 5'-phosphate (OMP), raises this reading to an absorbance of 0.8–0.9. The rate of absorbance decrease directly reflects the enzyme activity.

Eleven uracil auxotrophs were isolated from 108 colonies resistant to 5-fluoroorotic acid. Of these, four were defective for orotidine-5'-phosphate decarboxylase activity. Two of these had a low reversion frequency, $1.3 \times 10^{-7}$ and $<3.8 \times 10^{-9}$ respectively, and an absolute requirement for uracil. They were called SU-1 and SU-2, respectively.

d. Mutants other than Ura

1. Arginine. Of the twelve mutants, six had a tight phenotype. These were scored for growth on ornithine and citrulline. Mutants which cannot grow on either of these two intermediates of the arginine pathway are defective for either arginino-succinate synthase (arq1, arg10) or arginino-succinate lyase (aro4). One strain aro1-1 was unable to grow on either ornithine or citrulline and is therefore a candidate for a defect in ARG4.

2. Histidine. Thirty histidine mutants were isolated of which 12 had a tight phenotype suitable for transformation. The 12 mutants were assayed for histidinol dehydrogenase (HIS4) activity by the method of Martin et al. (1971), *Meth. Enzymol.* 17B:1–44. Three of the 12 were defective in this enzymatic activity and were therefore candidates for transformation. Mutant SH-1 had the lowest rate of reversion, $1.2 \times 10^{-7}$, a rate sufficiently low to permit screening for transformation.

3. Adenine. The majority of auxotrophs isolated had a requirement for adenine. Of these, 8 were pink, indicating a buildup of the pathway intermediate PR aminoimidazolesuccinocarboxamide which corresponds to a defect in either the ADE1 or ADE2 gene of *S. cerevisiae*. Two of the pink Ade. mutants were tight and are suitable as potential transformation hosts.

3. Construction of a *C. tropicalis* DNA Yep13 Library

The *C. tropicalis* 20336 (wild-type) gene library was constructed in *S. cerevisiae-E. coli* shuttle vector YEp13.

a. Isolation of *C. tropicalis* DNA

Large-scale preparations of DNA were prepared by a modification of the method of Cryer et al., (*Methods Cell. Biol.* (1975) 12:39). Yeast cells were grown in 100 ml of minimal medium (0.67% Yeast Nitrogen Base, 2% dextrose) to an $A_{600}$ of 1 to 2 and harvested by centrifugation at 2,000 ×g for 5 min. The cells were washed successively with 5 ml of $H_2O$, SED (1 M sorbitol, 25 mM EDTA, 50 mM dithiothreitol), and 1 M sorbitol and suspended in 5 ml of 1 M sorbitol-0.1 M Tris-HCl (pH 7.0). The cells were mixed with 50 to 100 ul of a 4 mg/ml solution of Zymolyase 60000 (Kirin Brewery (Japan)-distributed by Miles Scientific) and incubated at 30° C. for 1 hour to digest the cell walls. The spheroplast preparation was then centrifuged at 1,000 ×g for 5 to 10 min and suspended in lysis buffer (0.1% sodium dodecyl sulfate, 10 mM Tris-HCl [pH 7.4], 5 mM EDTA, 50 mM NaCl). Proteinase K and RNase A were each added to a concentration of 100 μg/ml, and the mixtures were incubated at 37° C. for 30 minutes. DNA was deproteinized by gently mixing the preparation with an equal volume of chloroform-isoamyl alcohol (24:1, v/v), and the phases were separated by centrifugation at 12,000 ×g for 20 min. The upper aqueous phase was drawn off into a fresh tube and extracted with an equal volume of PCA (phenol-chloroform-isoamyl alcohol, 25:24:1,v/v/v). The phases were separated as before, and the top phase was removed to a tube containing 2 to 3 volumes of cold (−20° C.) 100% ethanol. The sample was gently mixed, and DNA was collected by spooling onto a plastic rod. The DNA was immediately dissolved in 1 ml of TE buffer (10 mM Tris-HCl, pH 7.4, 1 mM EDTA) and dialyzed overnight against 100 volumes of 4° C. TE buffer.

b. DNA Library Construction

For the *C. tropicalis* DNA-YEp13 library construction, 200 μg of YEp13 (Broach, et al., (1979) *Gene* 8:121–133) was digested to completion with BamHI and treated with calf intestinal alkaline phosphatase as described by Maniatis et al. A 1 mg sample of wild-type *C. tropicalis* DNA was partially digested with 20 U of Sau3AI by incubation for 5, 6, 7, and minutes at 37° C. Fragments of 5 to 20 kb were size-selected by centrifugation through 5 to 20% sucrose gradients as described by Maniatis et al. A 1.6 μg sample of the vector and 30 μg of Sau3AI fragments were mixed and incubated overnight at 1° C. The ligated DNAs were transformed into *E. coli* by a modification of the CaCl₂ method of Mandel and Higa, (*J. Mol. Biol.* (1970) 53:159). The entire ligation reaction mix was added to 4.5 ml of competent *E. coli* MC1061 cells and then incubated on ice for 15 min. The mixture was shifted to 37° C. for 5 min after which 100 ml of LB medium was added, and the 37° C. incubation was continued for 1 hr. Ampicillin was then added to a concentration of 100 μg/ml, and the incubation continued for a second hour. Finally, the cells were centrifuged for 10 min at 3,000 ×g, resuspended in 1 ml of fresh LB medium, and spread in equal aliquots on 11 LB agar plates containing 100 μg/ml ampicillin. The approximately 20,000 colonies which resulted were scraped from the plates, and a portion of the cells was inoculated into 2L of the supplemented LB medium at a starting $A_{550}$ of 0.037. The culture was grown and plasmids were extracted. Under the ligation conditions used, approximately 98% of the colonies were tetracycline sensitive.

A second *C. tropicalis* genomic library was constructed using the following conditions: 0.8 μg of the vector and 15 μg of Candida Sau3AI fragments were mixed with 15 U of T4 DNA ligase and incubated overnight at 4° C. The ligation was then extracted with an equal volume of phenol/chloroform/isoamyl alcohol (25:24:1), ethanol precipitated, washed with 70% ethanol, and resuspended in TE buffer. All of the ligated DNA was added to 3.0 ml of competent *E. coli* MC1061 cells and incubated on ice for 15 min. The mixture was then shifted to 37° C. for 5 min after which time 60 ml of LB was added, and the 37° C. incubation was continued for one hour with shaking (225 rpm). The cells were spun for 25 minutes at 1,000 ×g, resuspended in a small volume of LB, and plated out onto 24 LB Amp plates. Approximately 20,000 colonies resulted from this transformation. They were scraped from the plates, and a portion of the cells was inoculated into 2 liters of LB Amp medium at a starting $A_{550}$ of 0.02. The culture was grown and plasmids were extracted as usual.

Assuming an average insert size of 10 kb and a genome size for *C. tropicalis* of about 10,000 kb then the two libraries combined represent 40 copies of the *C. tropicalis* geome. The probability of having any DNA sequence represented in the library is greater than 99%. [This figure is determined according to the formula of Clarke and Carbon (1976) *Cell* 9:91.]

4. Isolation of the URA3A Gene of *C. tropicalis*

After the isolation of a *C. tropicalis* URA3 gene, described herein below, it was discovered that a second functional URA3 gene existed that was distinguishable from the cloned gene by Southern blot restriction site analysis Therefore, the first gene isolated was designated URA3A, and is referred to as such in the description of its isolation provided below The second gene isolated was designated URA3B. Its isolation and characterization are described in Examples 9 through 13 DNA fragments containing the *C. tropicalis* URA3A gene were isolated from the *C. tropicalis* DNA library by their ability to complement a *S. cerevisiae* ura3 strain. To select plasmids with the URA3A gene, the *C. tropicalis* DNA library was mixed with spheroplasts of SHY-3, a his3 ura3 leu2 ade1 trp1 strain of *S. cerevisiae* (D. Botstein, *Gene* (1979) 8:17-24) Cells were allowed to regenerate on medium deficient in uracil. The transformation resulted in about 100 prototrophic yeast colonies per μg of library DNA for uracil selection. Colonies were picked from the agar and scored for additional auxotrophic markers. For SHY-3, all still required adenine, tryptophan, and histidine, but were Ura+ and Leu+, as would be expected, since the plasmid YEp13 carries the LEU2 gene.

Total yeast DNA was extracted from five Ura+ colonies and transformed into *E. coli*. Plasmid extracted from these transformants fell into two classes, with insert sizes of 6 kb and 10 kb, respectively. Restriction enzyme analysis revealed similarities in digestion patterns, indicating a region of overlapping homology within the two inserts which presumably included the URA3A gene. Upon retransformation into SHY-3, both plasmids complemented the uracil and leucine requirements of the host strain. The recombinant plasmid containing the 6kb insert and harboring the URA3A gene was designated pCU-1.

To confirm that the Ura+ colonies contained the *C. tropicalis* URA3A gene and not a DNA fragment with suppressor activity, the plasmids recovered from Ura+ cells were used to transform a uracil-requiring strain of *E. coli* (CSH 28; "Experiments in Molecular Genetics", J. Miller, 972, CSH) with a defect in the orotidine decarboxylase gene, pyrF, which corresponds to the URA3 gene in *S. cerevisiae*. Transformants were selected by their resistance to ampicillin and streaked onto synthetic medium plates (M9), one set supplemented with uracil and a second set lacking uracil. The transformants grew on the uracil-deficient plate. Thus, the identity of the gene encoded by the *C. tropicalis* DNA fragment in pCU-1 as a URA3 gene was confirmed.

5. Transformation of *C. tropicalis* with *C. tropicalis* URA3A Gene

An attempt was made to transform the ura3 strains of *C. tropicalis*, described in Example 2, Section C, with plasmids containing either the URA3A gene of *C. tropicalis* or the URA3 gene of *S. cerevisiae* with a region of DNA homologous to the *C. tropicalis* genome. Strains SU-1 and SU-2 were selected for transformation, since they both have a tight phenotype with a low reversion frequency and no background growth on uracil-deficient plates. As a positive control, *S. cerevisiae* strain SHY-3 was also transformed. The method used was adapted from a standard spheroplast transformation procedure.

A colony of *C. tropicalis* was inoculated into about 10 ml YEPD medium and the culture shaken at 30° C. overnight. Cells were diluted to $A_{600}$ equal to about 0.01-0.1 and the cells maintained in log growth phase in YEPD medium at 30° C. Then 0.03 ml of the culture at an $A_{600}$ of 0.01 was inoculated into 100 ml YEPD medium yielding at an $A_{600}$ of 0.00003, and the culture shaken at 30° C. overnight. After harvesting the culture at $A_{600}$ 0.2–0. 3 by centrifugation at 1500 ×g for 5 min, the cells were washed 1×10 ml sterile water, 1×10 ml freshly prepared SED (SED=1 M sorbitol, 25 mM EDTA, 50 mM DTT, filter sterilized), 1×10 ml 1 M sorbitol and the cells then resuspended in 5 ml SCE buffer (SCE=1.0 M sorbitol, 100 mM sodium citrate, pH 5.8, 10 mM EDTA). To the mixture was added 3 μl of 4 mg/ml Zymolyase 60000 and the medium was incubated at 30° C. Spheroplast formation was monitored as follows 100 μl aliquots of cells were added to either 900 μl of 0.2% SDS or 900 μl of 1 M sorbitol.

The incubation with the Zymolyase was terminated at the point at which cells lysed in SDS, but not in sorbitol (usually 15-30 min of incubation). At the termination of the incubation, the spheroplasts were washed 1×10 ml M sorbitol by centrifugation at 1,000 ×g for 10 min, 1×10 ml of sterile CaS (CaS=1 M sorbitol, 10 mM calcium chloride, filter sterilized) and the cells were then resuspended in a total of 0.6 ml of CaS.

Transformation was achieved by adding DNA samples (up to 20 μl) to 12×75 mm sterile polypropylene tubes; the DNA was in water or TE buffer. To each DNA sample was added 100 μl of spheroplast and the mixture incubated at room temperature for 20 min. To this mix was then added 1 ml of PEG solution (PEG solution=20% polyethylene glycol −3350, 10 mM calcium chloride, 10 mM Tris.HCl, pH 7.4, filter sterilized) and incubated at room temperature for 15 min. After centrifuging the samples at 1,000 ×q for 10 min, the PEG solution was decanted, the samples resuspended in 150 μl of SOS (SOS=1 M sorbitol, 30% YEPD medium, 10 mM calcium chloride, filter sterilized) and the resuspended samples were incubated for 30 min at room temperature. To the sample was then added 850 μl of sterile 1 M sorbitol.

For regeneration of cells, 10 μl and 990 μl aliquots of each sample were added to 10 ml aliquots of melted regeneration agar held at 50° C. and the mixture poured onto plates containing a solid 10 ml bottom agar layer of regeneration agar. (To prepare regeneration agar autoclave 9 g of bacto-agar and 13.5 g KCl in 240 ml of water, after autcloaving, 30 ml of 20% sterile dextrose and 30 ml of sterile 10X YNB is added and the mixture is then held at 55° C.) 10 ml of bottom layer agar was poured onto plates 30 minutes before the transformation samples were ready. Spheroplast formation was efficient, with an estimated 99% of the cells becoming osmotically fragile. Regeneration of protoplasts was efficient and was greater than 10%. Transformation of both ura3 strains of *C. tropicalis* occurred at a high frequency with the homologous gene preparations. In each case, the frequency of transformation was about 5,000-10,000 Ura+ colonies per microgram of DNA. Both closed circular and linear plasmid DNAs gave a high frequency of transformation. The efficiency was about 10- to 100-fold less using the LiCl transformation method.

*C. tropicalis* ura3 mutants were transformed to prototrophy using vectors containing the homologous URA3A gene. However, plasmids containing the *S. cerevisiae* URA3 gene did not transform *C. tropicalis* but did transform *S. cerevisiae*. Thus, the *S. cerevisiae* URA3 gene does not function in *C. tropicalis*.

6. Restriction Enzyme Map of the *C. tropicalis* DNA fragment Containing the URA3A Genet A 5.8 kb DNA fragment containing the gene was obtained from the YEp13-based *C. tropicalis* genomic library plasmid, pCU1. To facilitate restriction enzyme mapping of this fragment, most of the fragment was subcloned into pUC19 (Yanisch-Perron, C. et al., Gene (1985) 33:103–119). pUC19 is a small (2,686 basepair) pBR322- and M13mp19-based cloning vector containing a multiple cloning site, or polylinker. Restriction enzyme mapping and further subcloning of the insert were facilitated by the small size of the pUC19 and the presence of the polylinker. To construct this plasmid, a 6.2 kb EcoRI fragment from pCU1 containing mostly *C. tropicalis* DNA was inserted into the EcoRI site of pUC19, to produce plasmid pCU2. One end of the subcloned fragment contained 377 base pairs of YEp13, and the other stopped at an EcoRI site located approximately 50 base pairs from the right hand BamHI-Sau3AI junction. The restriction map of the subcloned DNA is presented in FIG. 1.

7. Localization of the URA3A Gene a. SU-2 Transformation with *C. tropicalis* DNA Fragments

A common and rapid method of mapping genes within DNA fragments of *S. cerevisiae* is to transform appropriate *S. cerevisiae* mutants with selected sub-fragments and determine if the sub-fragments can complement the mutant defect.

This technique was used to map the approximate position of the URA3A gene within pCU2. Serial transformations of the SU-2 strain were carried out with selected DNA restriction fragments derived from pCU2, as shown in FIG. 1. Fragments derived from the middle or right-hand end of the *C. tropicalis* DNA insert did not transform SU-2 to Ura+. However, an NruI-EcoRI fragment did transform SU-2 to uracil prototrophy. Additional DNA restriction fragments from the left-hand end of the insert were isolated and transformed into SU-2, as shown in FIG. 1. Each of these DNA fragments, a 2.1 kb ClaI, a 1.7 kb PstI-ClaI, a 2.3 kb PstI-SacI, and a 2.2 kb NruI-SacI, transformed SU-2 to Ura+. This confirmed the result that the URA3A gene is localized at the left-hand end of the insert.

b. Transformation of Plasmids Containing *C. tropicalis* DNA Fragments into *S. cerevisiae*

Since it would be possible for DNA fragments to transform SU-2 to prototrophy, but not contain the entire *C. tropicalis* URA3A gene, each was tested for URA3 function in a heterologous system. The *C. tropicalis* NruI-SacI, EcoRI-SacI, and ClaI fragments shown in FIG. 1 were subcloned into either pBR322 or pUC19, along with a DNA fragment containing a portion of the 2μ circle, which gives these plasmids the ability to replicate autonomously in *S. cerevisiae*. *C. tropicalis* URA3A subclones are shown in FIG. 1. Plasmids containing either the NruI-SacI (pCU3) or the EcoRI-SacI (pCU2 SacI) fragment transformed the *S. cerevisiae* ura3 strain, SHY3, to Ura+ but the plasmid containing the ClaI fragment did not. Therefore, the smallest *C. tropicalis* DNA fragment that contained the entire *C. tropicalis* URA3A gene was the NruI-SacI fragment, and the ClaI site was probably within the URA3A gene. Since it is believed that the URA3A gene mutation in SU-2 is very close to the KonI site and that the ClaI site is also within the URA3A gene, it appears that the *C. tropicalis* URA3A gene, which is assumed to be about the same size as that from *S. cerevisiae* (1.1 kb), exists mostly within this 0.88 kb CpaI-ClaI fragment.

8. Fate of Transformed URA3A DNA

Two classes of transformed colonies, either large or small, were observed when URA3A-containing DNA vectors were linearized within the *C. tropicalis* DNA insert and transformed into SU-2. The large colonies arise when the URA3A DNA vector integrates into the genome and becomes mitotically stable, whereas the small colonies result from autonomously replicating URA3 DNA vector sequences, which are unstable. Analysis of the *C. tropicalis* genonic DNA by Southern blot hybridization revealed the presence of two bands with homolgy to the cloned URA3A locus. One band represents the cloned URA3A locus whereas the other band represents a second DNA fragment with some but not complete homology with the cloned URA3A locus. To distinguish the two loci in the following discussions, they are referred to as URA3A, and URA3A. The fate of transformed DNA from the URA3A gene is described below.

Four transformants were initially analyzed by Southern blot hybridization. DNA was isolated from SU-2 strains transformed with pCU2 SacI linearized at the site within the URA3A gene. These genomic DNAs were then cut with either NcoI or HpaI. Neither of these restriction enzymes cut pCU2 SacI. A Southern blot filter was prepared from these digested DNAs and probed with labeled pCU2 SacI. Analysis of these transformants revealed three types of integration events. With type I, the banding pattern of transformed and wild-type DNA was identical. This type of transformant was interpreted to be the result of a gene conversion event. A gene conversion is the consequence of a double-crossover event at URA3A or a single-crossover event, followed by strand migration. The result is the incorporation of the wild-type URA3A sequences from the vector without other vector sequences. In type II and type III integration events, the band representing the locus was shifted to a position representing a larger DNA fragment. Integration types II and III are believed to be single and multiple-tandem integration events of wild-type URA3A sequences plus vector sequences at URA3A, respectively. In addition to these four transformants, ten other transformants were selected for analysis by Southern blot hybridization. Analysis of the blot showed that one gene conversion, six single-integration events, and three multiple-tandem integration events occurred. The blot also showed that all integration events occurred at the URA3A locus. Compiling the Southern blot results of the fourteen transformants examined showed the most common integration event was the single-copy integration of the transforming DNA. However, multiple-tandem integrations and gene conversions also occurred at a significant frequency. All integration events were directed to the URA3A locus and not the URA3B locus or any other loci in the genome. All integrative transformation events involved homologous recombination.

9. Isolation of URA3B gene of *C. tropicalis*

The approach taken to clone the URA3B sequence was to first build a genomic sublibrary of *C. tropicalis* DNA which contained the URA3B sequence, but not the URA3A gene. This sublibrary could then be probed with URA3A gene by colony hybridization. Since the URA3A gene would not be present in the sublibrary, the URA3A probe should only hybridize with the URA3B sequence.

Figure 2:
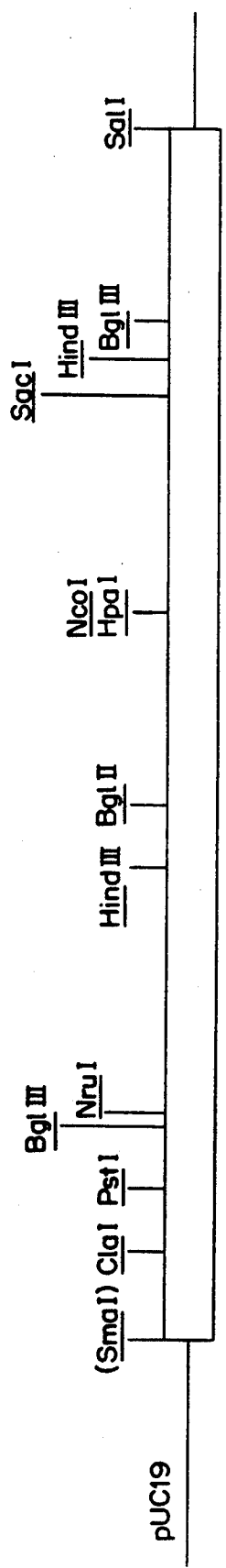
FIG. 2 shows the restriction enzyme map of the C. tropicalis URA3B-encoding insert in plasmid pCU4.

Southern blot hybridization analysis of restriction sites within *C. tropicalis* DNA revealed that the URA3B gene mapped within a 4.1 kb SalI-SmaI DNA fragment, whereas the URA3A gene was contained on a 6.6 kb fragment. To enrich for the desired 4.1 URA3B fragment in a *C. tropicalis* SalI-SmaI genomic DNA digest, several DNA fractions in the 3.0–5.0 kb size range were isolated. The fraction which contained the most URA3B DNA, as identified by Southern blot hybridization, was used to construct a *C. tropicalis* sublibrary in pUC19. Analysis of four hundred transformants by colony hybridization produced one transformant that hybridized to the URA3A probe. The plasmid isolated from this transformant contained a 4.1 kb SalI-SmaI insert, with a restriction enzyme pattern consistent with that predicted from the Southern hybridization data for the URA3B locus. This plasmid also hybridized with the URA3A probe, as revealed by Southern blot hybridization. It was therefore concluded that this plasmid, called pCU4, contained the URA3B locus. The restriction enzyme map of the pCU4 insert is presented in FIG. 2.

10. Transformation of Ura hosts with pCU4 DNA a. Transformation into the *C. tropicalis* ura3 strain SU-2

To test the URA3B locus for functional expression of URA3, pCU4 was transformed into the *C. tropicalis* ura3 strain, SU-2, by the standard spheroplast procedure. The plasmid was transformed in both uncut and linear forms (cut at ClaI site). This experiment resulted in transformation of SU-2 to prototrophy with both uncut and linear URA3B plasmid, at approximately the same transformation frequency achieved with the URA3A gene under the same conditions. This suggested that the URA3B sequence contained a functional URA3 gene.

b. Transformation into heterologous hosts

To further investigate the URA3 function of the URA3B fragment, the *C. tropicalis* URA3B plasmid (pCU4) was transformed into two heterologous ura3 hosts: the *E. coli* pyrF strain, CSH28, and the *S. cerevisiae* ura3 strain, SHY3. After transformation of pCU4 into CSH28 by selection for ampicillin resistance, eight URA3B transformants were tested for the ability to grow without uracil. All eight transformants were able to grow under this constraint. For testing URA3B function in *S. cerevisiae*, a DNA fragment containing a portion of the $2\mu$ circle, which gives plasmids the ability to replicate autonomously in *S. cerevisiae*, was first subcloned into the URA3B plasmid at the EcoRI site. Transformation of this plasmid, pCU4-$2\mu$, into SHY3 resulted in the transformation of the strain to prototrophy, at about the same transformation frequency as with circular URA3A plasmid. It was concluded that URA3B is a functional URA3 gene. The location of the coding sequence was determined by sequencing of the URA3B gene (see Section 12) and comparison of the URA3B sequence to that of the URA3A gene.

11. Fate of transformed URA3B DNA in *C. tropicalis*

When SU-2 was transformed with linearized URA3B DNA vectors, again two classes of transformed colonies, either large or small, were observed. It was assumed that the large and small colonies seen with the URA3B DNA vectors were the result of a similar effect, integrated versus autonomous vector sequence.

To determine the fate of transformed DNA, ten "large-colony" transformants were analyzed by Southern blot hybridization. DNA was isolated from SU-2 strains transformed with the URA3B-containing plasmid pCU4, linearized at the HpaI site. These genomic DNAs were then cut with both BamHI and SmaI, restriction enzymes which do not cut pCU4. A Southern blot filter was prepared from these digested DNAs and probed with labeled pCU4. The Southern revealed the same three types of integration events observed with URA3A DNA vectors (Example 8). The most common integration event with the linearized URA3B DNA vector was a single-copy integration of the transforming DNA. However, multiple-tandem integration and gene conversion also occurred at a significant frequency. All URA3B integration events were directed to the URA3B locus, and not the URA3A locus or any other loci in the genome. Thus, all integrative transformation events analyzed for URA3B involved homologous recombination. This finding is consistent with our earlier analysis of integration events for URA3A.

12. Sequence of *C. tropicalis* URA3A and URA3B genes

The URA3A and URA3B genes were sequenced by the Sanger dideoxy method, and the sequences are presented in FIG. 3 and FIG. 4, respectively.

13. Isolation of *C. tropicalis* HIS4 gene

*S. cerevisiae* strain 6657-9B (his4 leu2; Cregg et al. *Mol. Cell. Biol.* 5:3376-3385; 1985) was transformed with the *C. tropicalis* genomic library, described in Example 3, and the transformants were screened for histidine and leucine prototrophy. Nine His+ Leu+ colonies were identified and plasmid was recovered from three of the nine. Two of the plasmids were comprised of an 11.5 kb insert, and were called pCH1. The third plasmid appeared to be the library vector, YEp13, without insert DNA.

14. Transformation of *C. tropicalis* and *S. cerevisiae* with pCH1

Plasmid pCH1 was again used to transform the his4 leu2 *S. cerevisiae* strain to a His+ Leu+ phenotype. In addition, pCH1 transformed the His4−*C. tropicalis* strain SH-1 to His+ at a high frequency (approximately $10^3$ isolates/ug DNA). These data indicated that the 11.5 kb insert in pCH1 contained a *C. tropicalis* HIS4 gene and that it could be used to transform SH-1 to histidine prototrophy at a high frequency.

15. Characterization of HIS4 gene

A 6.5 kb SphI fragment, derived from pCH1 and containing mostly *C. tropicalis* DNA, was sub separately into pUC18, yielding pCH2, and into the p plus 2 μ circle vector, yielding pCH2μ. (A DNA fragment, containing a portion of the 2 μ circle, which gives plasmids the ability to replicate autonomously in *S. cerevisiae*, was subcloned into pUC18, yielding vector pUC18 plus 2μ circle.) A restriction enzyme map of this fragment is presented in FIG. 5. One end of the subcloned fragment contained 185 base pairs of YEp13, and the other stopped at an SphI site approximately 5000 base pairs from the left-hand BamHI-Sau3AI junction of the vector with the insert DNA.

Plasmids pCH2 and pCH2μ were separately used to transform the *C. tropicalis* and *S. cerevisiae* his4 mutants (SH-1 and 6657-9B, respectively) to prototrophy, which indicated that the 6.5kb SohI fragment contained the *C. tropicalis* HIS4 gene.

To further localize the *C. tropicalis* HIS4 gene, fragments derived from pCH2 were subcloned into pUC18, or pUC18 plus 2μ circle, or both vectors. The inserts and resulting vectors were as follows:

| Insert | Resulting Vector |
| --- | --- |
| 6.5 kb SphI | pCH2 |
| 5.2 kb SphI-SalI | pCH2B SalI |
| 5.0 kb EcoRI-SphI | pCH3 |
| 4.1 kb BamHI-SalI | pCH4 |

These subclones were separately transformed into either the *C. tropicalis* or *S. cerevisiae* his4 mutant host cells and screened for histidine prototrophy. The data, shown in FIG. 5, indicated that the smallest fragment which could transform the *S. cerevisiae* mutant to His+ was the 4.1 kb BamHI-SalI fragment contained in vector pCH4.

Figure 5:
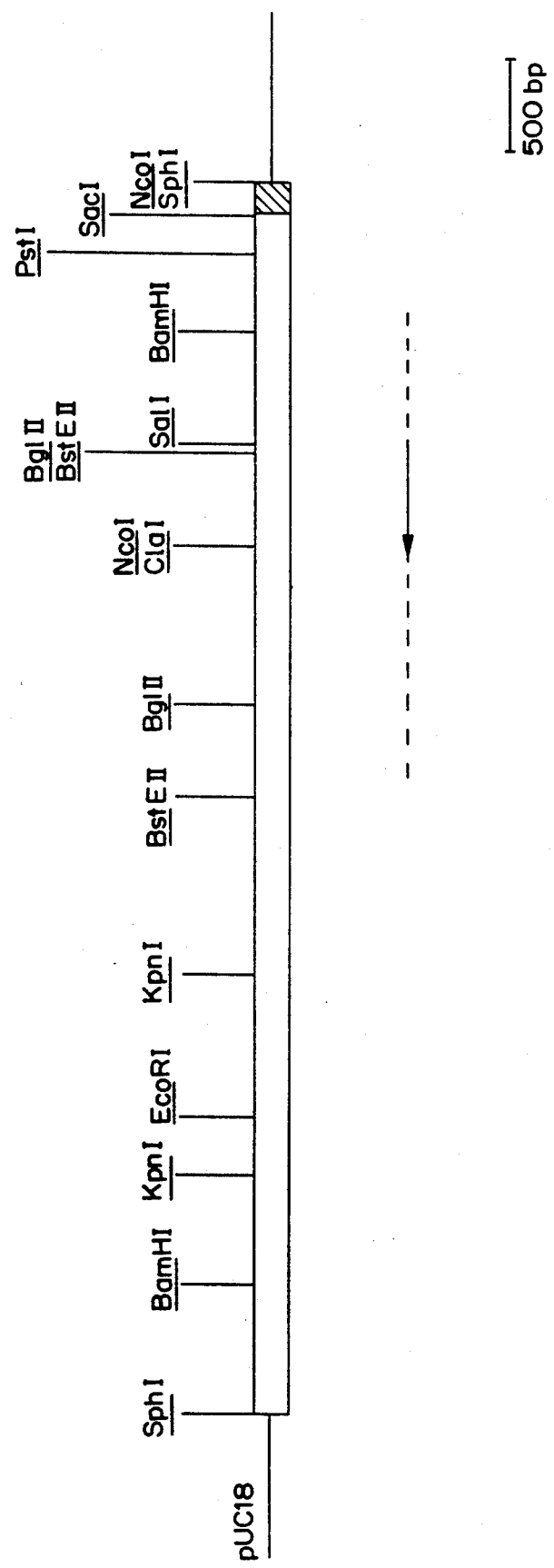
FIG. 5 shows the restriction enzyme map of the C. tropicalis HIS4-encoding insert in plasmid pCH2.

Preliminary sequence analysis of a DNA fragment near the SalI site of pCH4 has revealed the location of the *C. tropicalis* HIS4 gene by virtue of its homology with the *S. cerevisiae* HIS4 gene sequence. The sequenced *C. tropicalis* HIS4 fragment is 196 bp long, has 72% homology at the nucleotide level and 87% homology at the amino acid level with the *S. cerevisiae* HIS4 gene. The location of the gene within the pCH2 insert, as suggested by the DNA sequence, is shown in FIG. 5. A portion of the sequence of the *C. tropicalis* HIS4 gene and comparison to the *S. cerevisiae* HIS4 gene sequence is provided in FIG. 6. The sequence is clearly distinguishable from the *S. cerevisiae* HIS4 gene sequence. Plasmid pCH3, which has a 5.0 kb EcoRI-SphI insert, is the smallest subclone containing the entire *C. tropicalis* HIS4 gene. pCH2B SalI and pCH4 are missing approximately the last 600 base pairs of the HIS4 gene. It is likely that these two subclones yield transformants with a slower growth rate because they are missing part of the HIS4 gene and produce a defective enzyme.

16. Fate of Transformed HIS4 DNA in *C. tropicalis* a. Colony Size of Transformants

When the *C. tropicalis* his4 mutant (SH-1) was transformed with the HIS4 DNA vector pCH2B SalI linearized at the ClaI site, two classes of transformed colonies, either large or small, were observed. The large colonies resulted when the DNA vector integrated into the genome and became mitotically stable, whereas the small colonies result from autonomously replicating DNA vector sequences which are unstable.

As with the URA3 DNA vectors, it was of interest to demonstrate homologous recombination of the HIS4 DNA vector in *C. tropicalis*. Therefore, only large colonies with presumably integrated sequences were examined further.

b. Southern Blot Analysis of Transformants

To determine the fate of transformed DNA, ten "large-colony" transformants were analyzed by Southern blot hybridization. DNA was isolated from the SH-1 strains transformed with the HIS4 containing plasmid, pCH2B SalI, linearized at the ClaI site. These genomic DNAs were then cut with HpaI, a restriction enzyme which does not cut pCH2B SalI. A Southern blot filter was prepared from these digested DNAs and probed with a labeled BamHI-SalI fragment derived from pCH2B SalI. Analysis of these transformants revealed the same three types of integration events observed with URA3A and URA3B DNA vectors, that is gene conversions (type I), single vector insertion at HIS4 (type II) and multiple tandem repeat vector insertion at HIS4 (type III). Thus, as seen at the URA3 loci, recombination at HIS4 occurred by homology between sequences shared by vector and host. A further observation of the type II and type III HIS4 transformants was that, in addition to the Southern blot band expected for these types, a band always remained at the position of the untransformed HIS4 locus. The presence of this latter band indicates that *C. tropicalis* genome is diploid for the HIS4 locus. The URA3 loci, which appear to be an exception, are probably alleles of one gene in a chromosomal region in which diploid homologs have undergone significant divergence in DNA sequence. The conclusion that *C. tropicalis* is diploid is consistent with a published report (Gaillardin, C. and Heslot, H. (1971). Physiological and genetical studies on yeasts of the genus Candida. *In: Radiation and Radioisotopes for Industrial Microbiology*. International Atomic Energy Agency Publication SM-134/5 pp.93-111.)

It is evident from the above results that an efficient transformation system is provided for production of a wide variety of products by *C. tropicalis*. Because of the unique features of *C. tropicalis*, for example its alkane and fatty acid utilization, its peroxisomal system, various products of interest can be produced employing these features of *C. tropicalis*. In addition, because of its ability to be fermented and its desirable growth characteristics, compounds which can be produced in other hosts may also be more efficiently produced in the *C. tropicalis* system. Vectors are provided which impart prototrophy to the auxotrophic hosts, so as to provide a prototrophic system, which does not require addition of expensive metabolites, is self-policing in that cells which lose the construct will be overgrown by the cells which contain the construct, and the auxotrophic cells have a low reversion frequency. All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference. Living cultures of strain SU-2 (ATCC 20913) and SH-1 (ATCC 20952) and *E. coli* (HB101) containing plasmid pCU1 (ATCC 67867), *E. coli* (MC1061) containing plasmid pCU4 (ATCC 67966), and *E. coli* (MC1061) containing plasmid pCH2 (ATCC 67965) have been deposited with American Type Culture Collection, 12301 Parklawn Drive, Rockville, Md. 20852.

The invention now being fully described, it will be apparent to one of ordinary skill in the art that many changes and modifications can be made thereto without departing from the spirit or scope of the appended claims.

What is claimed is:

1. A method for transforming *Candida tropicalis* comprising:
   (1) providing an auxotrophic host which requires uracil for growth due to a lack of orotidine-5'-phosphate decarboxylase as the result of mutations in the URA3A and RUA3B genes; (2) enzymatically treating the cell wall of said auxotrophic host; (3) adding to the resulting spheroplasts a DNA construct comprising the *C. tropicalis* URA3A or URA3B genes and which functionally compliments the auxotrophic mutation in said host; (4) fusing said DNA construct with said auxotrophic host to form transformed cells; (5) selecting said transformed cells by their ability to grow in a selective medium lacking uracil.

2. An auxotrophic host according to claim 1 wherein said host is *C. tropicalis* SU-2.

3. The *C. tropicalis* URA3A gene according to claim 1 wherein said gene is from pCU1.

4. The *C. tropicalis* URA3B gene according to claim 1 wherein said gene is from pCU4.

5. A transformed *Candida tropicalis* host derived from *C. tropicalis* SU-2 which is prototrophic as the result of transformation with either the URA3A or URA3B gene.

6. A method for transforming *Candida tropicalis* comprising: (1) providing an auxotrophic host which required histidine for growth due to a lack of histidinaol dehydrogenase as the result of mutations in both HIS4 genes; (2) enzymatically treating the cell wall of said auxotrophic host; (3) adding to the resulting spheroplasts a DNA construct comprising the *C. tropicalis* HIS4 gene which functionally compliments the auxotrophic mutation in said host; (4) fusing said DNA construct with said auxotrophic host to form transformed cells; (5) selecting said transformed cells by their ability to grow in a selective medium lacking histidine.

7. An auxotrophic mutant according to claim 6 wherein said strain is *C. tropicalis* SH-1.

8. The *C. tropicalis* HIS4 gene according to claim 6 wherein said gene is from pCH2.

9. A transformed *Candida tropicalis* host derived from *C tropicalis* SH-1 which is prototrophic as the result of transformation with the *C. tropicalis* HIS4 gene.

* * * * *